United States Patent
Zollinger et al.

(10) Patent No.: US 7,871,368 B2
(45) Date of Patent: Jan. 18, 2011

(54) APPARATUS, SYSTEM, AND METHOD FOR APPLYING AND ADJUSTING A TENSIONING ELEMENT TO A HOLLOW BODY ORGAN

(75) Inventors: Chris Zollinger, Chino Hills, CA (US); Vaso Adzich, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 51 days.

(21) Appl. No.: 12/286,978

(22) Filed: Oct. 3, 2008

(65) Prior Publication Data
US 2009/0043153 A1    Feb. 12, 2009

Related U.S. Application Data

(63) Continuation of application No. 11/371,599, filed on Mar. 9, 2006, now Pat. No. 7,431,692.

(51) Int. Cl.
*A61F 2/00* (2006.01)
(52) U.S. Cl. ....................................................... 600/37
(58) Field of Classification Search ................... 600/16, 600/37; 623/2.1, 2.11, 2.16
See application file for complete search history.

(56) References Cited

U.S. PATENT DOCUMENTS

| | | | |
|---|---|---|---|
| 5,571,215 A | 11/1996 | Sterman et al. | |
| 6,099,547 A | 8/2000 | Gellman et al. | |
| 6,129,758 A | 10/2000 | Love | |
| 6,332,893 B1 | 12/2001 | Mortier et al. | |
| 6,629,534 B1 | 10/2003 | St. Goar et al. | |
| 6,629,921 B1 | 10/2003 | Schweich et al. | |
| 6,719,786 B2 | 4/2004 | Ryan et al. | |
| 6,726,715 B2 | 4/2004 | Sutherland | |
| 7,144,363 B2 * | 12/2006 | Pai et al. ...................... | 600/16 |
| 7,252,632 B2 * | 8/2007 | Shapland et al. .............. | 600/37 |
| 2002/0042651 A1 | 4/2002 | Liddicoat et al. | |
| 2002/0161378 A1 | 10/2002 | Downing | |

(Continued)

FOREIGN PATENT DOCUMENTS

WO    WO 97/30649    8/1997

(Continued)

OTHER PUBLICATIONS

PCT International search report for International Patent Application No. PCT/US2007/006052, Filed Aug. 3, 2007.

*Primary Examiner*—Charles A Marmor, II
*Assistant Examiner*—Christine D Hopkins
(74) *Attorney, Agent, or Firm*—Richard B. Cates; David L. Hauser

(57) ABSTRACT

An adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

20 Claims, 8 Drawing Sheets

U.S. PATENT DOCUMENTS

| | | |
|---|---|---|
| 2003/0078465 A1 | 4/2003 | Pai et al. |
| 2003/0078653 A1 | 4/2003 | Vesely et al. |
| 2003/0083742 A1 | 5/2003 | Spence |
| 2003/0105519 A1 | 6/2003 | Fasol et al. |
| 2003/0167062 A1 | 9/2003 | Gambale et al. |
| 2003/0181940 A1 | 9/2003 | Murphy et al. |
| 2004/0003819 A1 | 1/2004 | St. Goar et al. |
| 2004/0024414 A1 | 2/2004 | Downing |
| 2004/0024451 A1 * | 2/2004 | Johnson et al. ............ 623/2.11 |
| 2004/0024452 A1 | 2/2004 | Kruse et al. |
| 2004/0034380 A1 | 2/2004 | Woolfson et al. |
| 2004/0037813 A1 | 2/2004 | Simpson et al. |
| 2004/0044350 A1 | 3/2004 | Martin et al. |
| 2004/0073301 A1 | 4/2004 | Donlon et al. |

FOREIGN PATENT DOCUMENTS

| | | |
|---|---|---|
| WO | WO9911201 | 3/1999 |
| WO | WO 2005/110244 | 11/2005 |

* cited by examiner

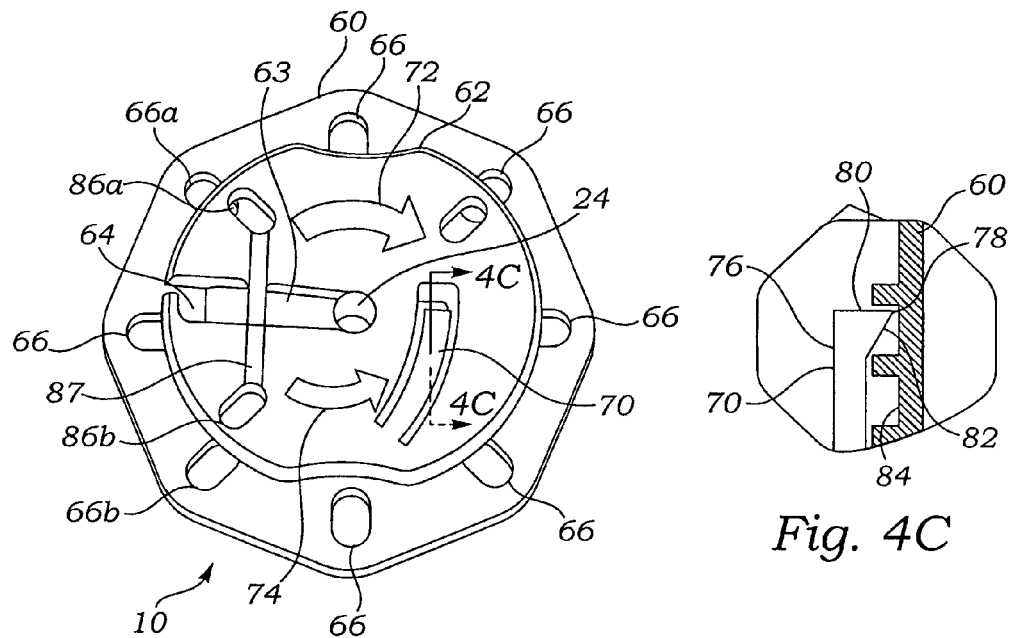
*Fig. 4A*
*Fig. 4C*
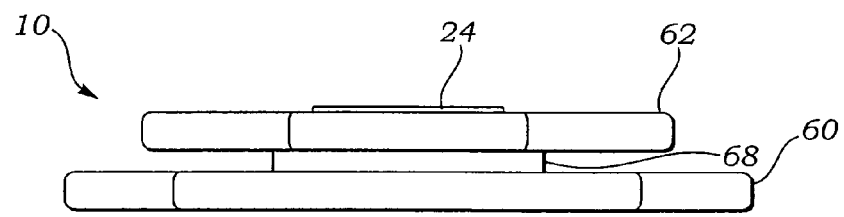
*Fig. 4B*

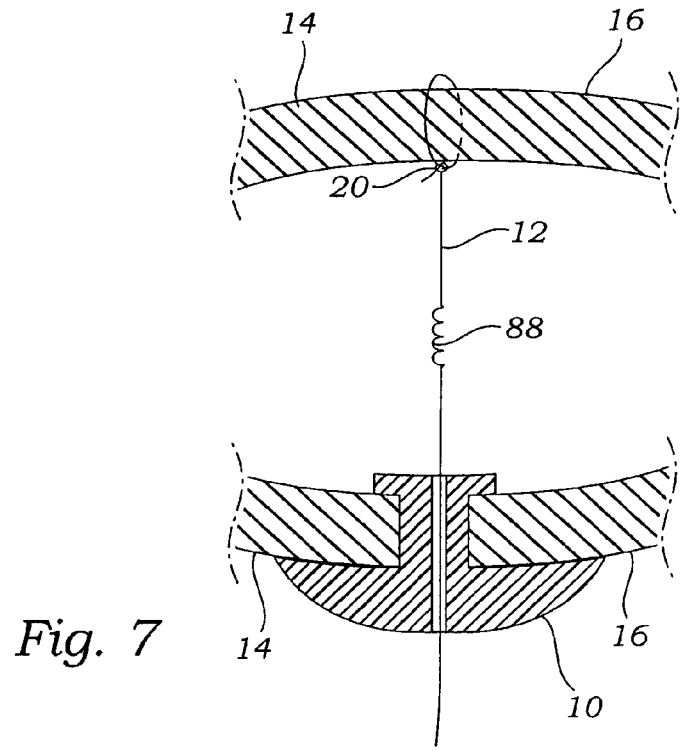
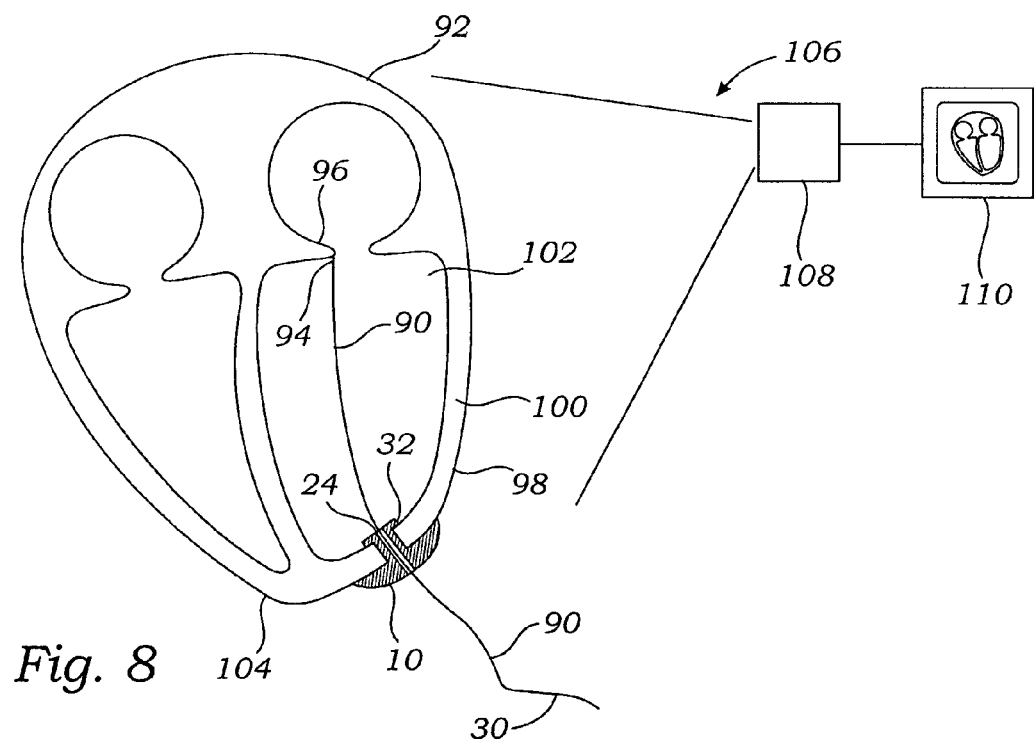
Fig. 7
Fig. 8

APPARATUS, SYSTEM, AND METHOD FOR APPLYING AND ADJUSTING A TENSIONING ELEMENT TO A HOLLOW BODY ORGAN

RELATED APPLICATIONS

The is a continuation of U.S. patent application Ser. No. 11/371,599, filed Mar. 9, 2006, now U.S. Pat. No. 7,431,629 and entitled, "Apparatus, System, and Method for Applying and Adjusting a Tensioning Element to a Hollow Body Organ," the entire contents of which are hereby incorporated by reference herein.

FIELD OF THE INVENTION

The present invention relates generally to medical devices and particularly to applying and adjusting tensioning elements to a body organ.

BACKGROUND OF THE INVENTION

A variety of surgical procedures use tensioning elements to effect repair of a body organ. For example, heart disease can be treated with such tensioning elements, which can be used to replace and/or assist the functioning of native structures.

One type of heart disease occurs when a ventricle becomes dilated. Ventricular dilatation can reduce the heart's ability to pump blood, and can lead to a significant increase in wall tension and/or stress. Such wall tension and/or stress can lead to further dilatation, which can lead to heart failure. One method of treating this condition is to apply tensioning elements to the heart wall which absorb some of the tension produced during heart operation, thereby reducing the tension in the heart wall. Determining the proper tension to apply via the tensioning elements can be difficult.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Valve disease often involves damaged chordae tendineae, which are thread-like bands of fibrous connective tissue that attach to the mitral or tricuspid valve at one end and to the papillary muscles or the ventricular wall at the other end.

Various surgical techniques may be used to repair a diseased or damaged heart and/or heart valve. One method for treating defective valves is through repair or reconstruction. A repair technique that has been shown to be effective in treating incompetence is annuloplasty, in which the effective size and/or shape of the valve annulus is modified by securing a repair segment, such as an annuloplasty ring, around the heart valve annulus. For example, the valve annulus may be contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity to prevent reverse flow while permitting good hemodynamics during forward flow.

In many diseased valves, the chordae tendineae are either ruptured, otherwise damaged, or of an improper length. When chordae tendineae are too long, too short, or otherwise damaged, the corresponding tricuspid or mitral valve to which they are attached typically may fail to close properly. For example, chordae tendineae which are ruptured or are too long allow a valve to prolapse, wherein one or more valve leaflets swing backward past their proper closed position. This can lead to regurgitation, which is the unwanted backflow of blood from a ventricle to an atrium resulting from imperfections in the valve. When the valve allows such backward flow into an atrium, the corresponding ventricle must pump progressively harder to circulate blood throughout the body, which in turn promotes congestive heart failure.

Repairing and/or replacing dysfunctional chordae tendineae has been performed for some time. The techniques for such repair are often complicated due to the difficulties in accessing the surgical site, in identifying the dysfunctional chordae tendineae, and in determining the proper length for the repaired and/or replacement chordae tendineae. Determining the proper length for replacement chordae tendineae can be a complex procedure. Additionally, prior methods for replacing and adjusting the length of the chordae tendineae often involved making such adjustments on an arrested heart, whereas the final test of the appropriateness of the adjusted length is typically performed while the heart is beating. Accordingly, what has been needed is a method of adjusting replacement chordae lengths on a beating heart.

Accordingly, there has been a need for an improved apparatus, system, and method to apply and adjust tensioning members on and/or in a body organ, including the repair and replacement of chordae tendineae on heart valves. The present invention satisfies one or more of these needs.

SUMMARY OF THE INVENTION

The present application is generally described with respect to its use in the repair of the mitral valve, which regulates blood flow from the left atrium (LA) to the left ventricle (LV), and more specifically in the replacement of chordae tendineae. However, the invention could also be applied to treatment of other body structures where application of an adjustable tensioning device is desired.

The invention includes an adjustable support pad system. The adjustable pad includes one or more adjustable securing elements, with each securing element configured to retaining an end of a suture line or other tensioning element. The securing element is adjustable, so that the tension applied to the suture line can be adjusted. In one embodiment the securing element is a rotatable spool-like structure about which the suture line can be wound. The spool can be rotated in one or more directions to increase and/or reduce the tension in the suture line. The securing element may include a locking mechanism, such as a ratchet, segmented coil, clip, and/or cam.

The adjustable pad is configured to be attached to the outside of the organ. In use, the adjustable pad is sutured or otherwise secured to the outside of a body organ, with a tensioning element (such as a suture line) passing from the adjustable pad, into the body organ, and to an opposing attachment point. A first end of the suture line is secured to the tensioning element, and the second or opposing end of the suture line is attached to the opposing attachment point. The opposing attachment point may be inside or outside the body organ.

In an embodiment, the adjustable pad can be sutured or otherwise attached to the outside of the ventricle of a human heart. The adjustable pad is configured to provide a supporting structure for one end of the suture line or other tensioning element, thereby protect the organ wall from damage that might occur if the suture line were attached directly to the organ wall. The adjustable pad also provides the ability to adjust the length of (and thereby the tension in) the suture line, without having to retie either end of the suture line. With the adjustable pad positioned on the outside of a human heart, a surgeon could thus adjust the tension while the heart is beating, thus permitting the surgeon to see the functioning of the heart (and hence the effectiveness of the current tension setting in repairing heart function) in real time via echocardiography or other imaging techniques while he or she is adjusting the tension in the suture line or other tensioning element.

The invention can be used for correction of mitral valve prolapse using replacement chordae, such as expanded neochordae suture (such as polytetrafluroethylene (e-PTFE)). One or more replacement chordae sutures can be passed from an adjustable chordal pad, through the heart wall, and then tied in position on the desired leaflet. This part of the procedure could also be reversed, with one or more replacement chordae sutures tied to the leaflet and passed through the heart wall to an adjustable chordal pad. The desired number and length of the replacement chordae depend on the needs of the particular patient, including characteristics of the valve annulus, the valve leaflets, and the existing chordae. This portion of the procedure can be performed on a beating or arrested heart.

With the replacement chordae in place, the surgeon can adjust the chordae length from the outside of the heart by adjusting the adjustable chordal pad. In one embodiment, the adjustable chordae pad includes an adjustable tensioning element in the form of a spool-like structure that can have an end of one or more replacement chordae wound therearound. By rotating the spool-like structure in one direction or the other, the surgeon or other user can shorten (tighten) or lengthen (loosen) the replacement chordae. Depending on the particular application, one or more adjustable chordal pads may be used on a patient's heart. Additionally, the adjustable support pad may have one or more separate spools, each of which may be separately adjustable from the other spools. With separate replacement chordae wound upon separately adjustable spools on a single support pad, the support pad serves as a platform for multiple replacement chordae.

The apparatus can be used in conjunction with other repair procedures on the particular body organ or body structure involved. For example, replacing chordae tendineae can be combined with application of a heart valve annuloplasty ring or other techniques that can reshape the heart valve annulus to a desired shape, and/or prevent the heart valve annulus from further and undesired deformation. Moreover, the invention is not limited to heart treatments. Other organs and body structures could also be treated. For example, the invention could be used to apply tension to treat a pelvic organ prolapse, to reinforce muscles, and/or to reshape a body structure.

The apparatus may include a flange and/or cannula that passes into the body organ and which may provide a protective surface between the organ wall and the tensioning element.

Various aspects of the invention can be used individually or in combination to repair a body organ. The invention is applicable to various ways of accessing the organ for repair, including an open surgical approach or a minimally-invasive approach such as percutaneous or intercostal.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIG. 4A depicts a top view of an adjustable support pad according to a further embodiment of the invention;

FIG. 4B depicts a side view of the apparatus of FIG. 4A;

FIG. 4C depicts a side view, in close up and partial cross-section, of a portion of the apparatus of FIGS. 4A and 4B;

FIG. 7 depicts a side view, in partial cross-section, of a further embodiment of the invention; and FIG. 8 depicts a side view, in partial cross-section, of a system and method for applying replacement chordae to a human heart according to an embodiment of the invention;

DETAILED DESCRIPTION OF THE INVENTION

Figure 1:
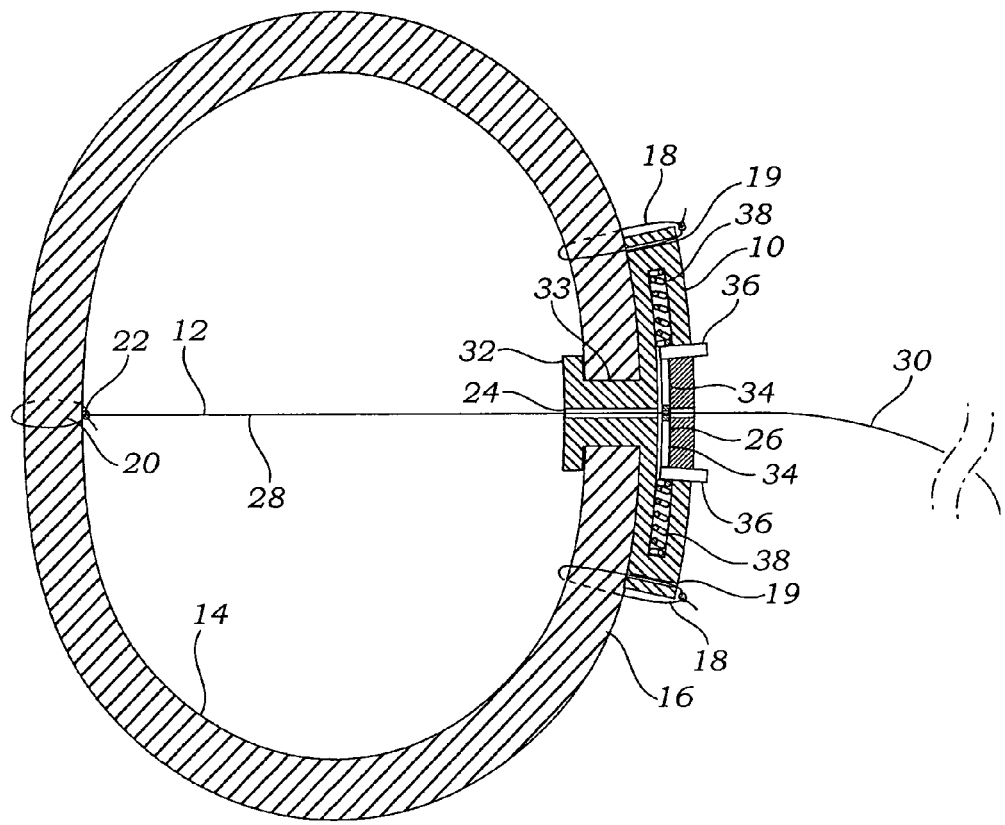
FIG. 1 depicts a side view, in partial cross-section, of a device having a tensioning element for application to a body organ according to an embodiment of the invention.

FIG. 1 depicts an adjustable support pad 10 according to an embodiment of the invention with a tensioning element in the form of a suture line 12 under tension within an organ 14. The adjustable support pad 10 is placed against the outside of the organ wall 16 and secured thereto via ordinary sutures 18 passing through suture holes 19 on the support pad 10. The suture line 12 is secured to an attachment point 20 via a suture knot 22. The suture line 12 passes from the attachment point 20 through a hole 24 in the adjustable pad 10 to a locking mechanism 26. With the suture line 12 secured to the adjustable support pad 10, the suture line 12 will have a tensioned portion 28 passing from the attachment point 20 to the adjustable support pad 10, and a slack portion 30 which is past the adjustable support pad 10.

In the particular embodiment of FIG. 1, the adjustable pad 10 includes a protective flange 32 which surrounds the pad hole 24 and is secured to a generally tubular cannula 33 that passes through the organ wall 16. The protective flange 32 and cannula 33 may serve to protect the suture line 12 and/or organ wall 16 from contact therebetween. Note that the flange 32 and/or cannula 33 could be left off of the device, as in the embodiment of FIGS. 2A and 2B, so that the pad could be secured directly to the organ wall without the pad itself puncturing or otherwise passing through the organ wall. The choice of whether to include the flange 32 and/or cannula 33 depends on the particular application.

The locking mechanism can comprise one or more mechanisms that engage the suture to prevent its movement in one or more directions. For example, in the embodiment of FIG. 1, the locking mechanism 26 comprises two movable engagement structures 34 that engage against the suture line 12 to prevent it from moving with respect to the adjustable pad 10. The movable engagement structures 34 engage against movable control buttons 36 which a user can use to move the movable engagement structures 34 into or out of engagement with the suture line 12. The device further includes springs 38 which bias the movable engagement structures 34 into engagement with the suture line 12, thereby biasing the locking mechanism 26 to the locked position whereby movement of the suture line is prevented in one or more directions. In the particular embodiment of FIG. 1, movement of the suture line 12 is prevented in both directions (i.e., into the organ and out of the organ) when the movable engagement structures 34 engage the suture line 12. Although the embodiment depicted includes two movable engagement structures 34 in opposition to each other, other numbers of movable engagement structures are within the scope of the invention. For example, a single such movable engagement structure could be used without a second opposing movable engagement structure. Such a single movable engagement structure could be combined with an opposing but non-movable engaging structure, depending on the particular application.

In some applications, fluid leakage out of the organ 14 through the pad hole 24 may be of concern. In many cases the tightness of the pad hole 24 about the suture line 12 can prevent such leakage. Natural bodily sealing processes, such as blood clotting and/or tissue ingrowth in front of or into the pad hole 24, can further prevent such leakage. The pad hole 24 may include a sealant (not shown) against such leakage, such as a biocompatible sealant positioned within the pad hole 24. Sizing the pad hole 24 so that the suture line 12 just fits therethrough, without substantial spacing between the suture line 12 and the walls of the pad hole 24, will also help to prevent leakage. The walls of the pad hole 24 could also be formed from flexible and/or padded material that places some inward pressure against the suture line 12, thereby preventing fluid leakage. For example, a compressible material such as silicon or another compressible polymer could form all or part of the walls of the pad hole 24, and would press inwardly against the suture line 12 if the pad hole 24 was sized correctly, e.g., sized with a diameter that will compress against the suture line 12 to prevent leakage around the suture line 12. The walls of the pad hole 24 might also be formed of, or lined with, a biocompatible material that encourages tissue ingrowth, so that the tissue ingrowth acts to block leakage. Additionally, the locking mechanism itself may help to prevent such leakage, in that the locking mechanism, depending on the particular embodiment, may block all or a substantial portion of the pad hole 24 that is not already taken up by the suture line 12. In another embodiment, the flange or other material in the support pad through which the suture is intended to pass could be solid (i.e., without a pre-formed pad hole therethrough) material, in which case the user could create a pad hole using a suturing needle through which the suture was threaded. The user would drive the suture-threaded needle through the material, thus creating the pad hole and passing the needle and suture assembly through the newly-created pad hole in the adjustable support pad. The suture would thus penetrate the flange or other material, creating a hole only large enough for the suture material. If compressible material were involved, the compressible material could engage against the small suture hole to further prevent leakage.

Figure 2A:
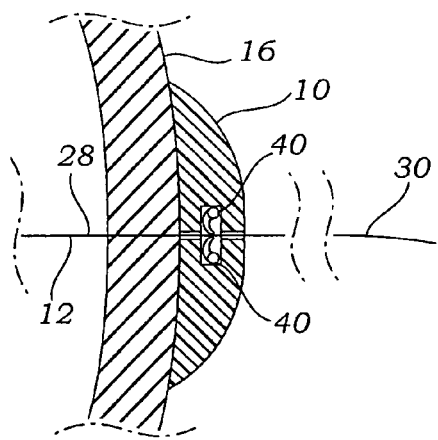
FIG. 2A depicts a side view, in partial cross-section, of a further embodiment of the invention.
Figure 2B:
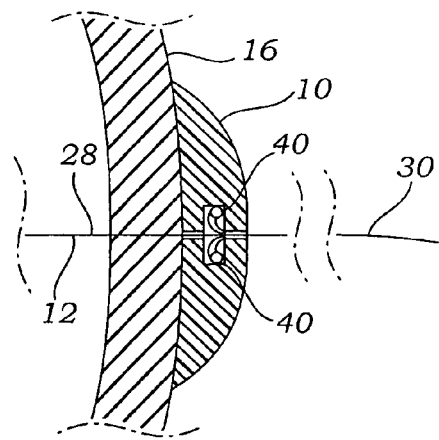
FIG. 2B depicts a side view, in partial cross-section, of the device of FIG. 2A with the cams in the open position.

FIGS. 2A and 2B depict a further embodiment of the invention, wherein an adjustable support pad 10 includes a locking mechanism formed by two movable engagement structures in the form of opposing cams 40. In FIG. 2A the cams 40 are in the locked or engaging position wherein longitudinal movement of the tensioning line 12 is prevented, but in FIG. 2B the cams 40 are rotated to their open or unlocked position. The cams 40 may be biased by springs or other biasing devices [not shown] toward the closed position, but such bias may not be needed where the tension in the tensioned side 28 of the tensioning line 12, combined with contact with the cams 40 against the tensioning line 12 as is passes through the cams 40, pulls the cams 40 to their closed position.

Note that the particular embodiment of FIGS. 2A and 2B does not include the flange and cannula (elements 32 and 33 in FIG. 1). Accordingly, while the tensioning line 12 passes through the organ wall, the adjustable support pad 10 is secured directly to the outside of the organ wall and does not puncture or otherwise pass through the organ wall.

Figure 3A:
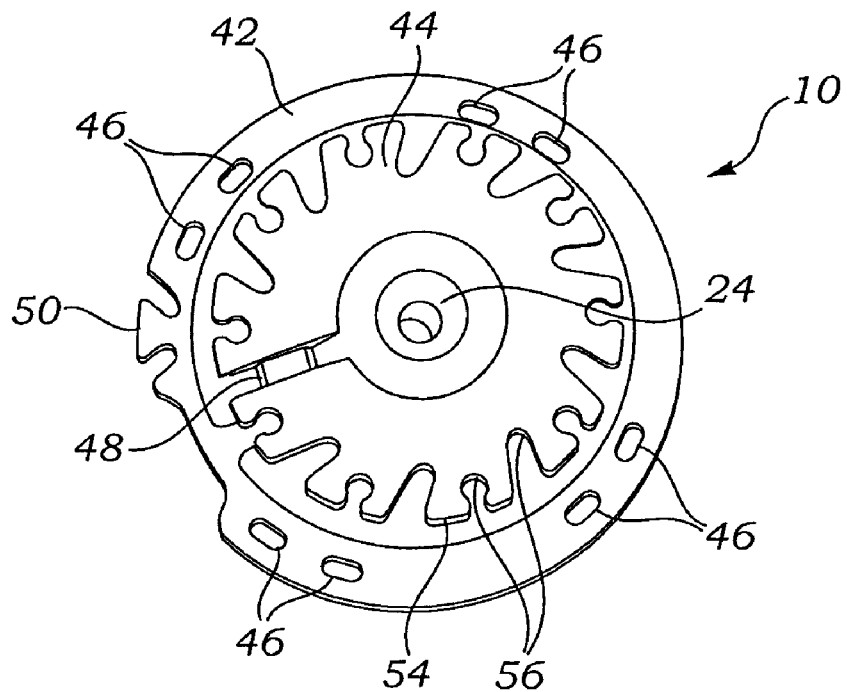
FIG. 3A depicts a top view of an adjustable support pad according to a further embodiment of the invention.

FIGS. 3A and 4B depict a further embodiment of the invention, with an adjustable support pad 10 having a lower "fixed" portion 42 and an upper rotatable portion 44. The support pad 10 includes several sets of suture holes 46 through which suture can be passed to suture the support pad 10 to the surface of an organ wall. The tensioning line 12 passes up through the pad hole 24, across the upper portion 44 and down through the suture slot 48, and is then secured to a suture tie point 50. With the tensioning element 12 thus secured to the support pad 10, the user can rotate the upper portion 44, which will cause the tensioning element 12 to be tightened as it is wrapped about a center spindle 52, which in the embodiment of FIG. 3A is positioned on the upper portion 44 and will rotate therewith. Note, however, that the spindle could be fixed to the lower portion 42 of the adjustable support pad 10, in which case the spindle would not rotate as the tensioning line 12 was wound thereon. In use, the surgeon or other user secures the support pad 10 to the organ wall (which can be accomplished via suture or other suitable attachment means), leads the tensioning line 12 through the pad hole 24 into the suture slot 48, ties off the tensioning line 12 to the tie point 50, adjusts the tension in the tensioning line 12 by rotating the upper rotatable portion 44 until the desired tension is achieved (which can be confirmed by monitoring the organ characteristics during tensioning via an imaging system such as echocardiography), and then secures the upper rotatable portion 44 in a fixed position so that it will not take in or let out any additional tensioning line 12. The order of these steps could be varied, depending on the particular application.

Figure 3B:
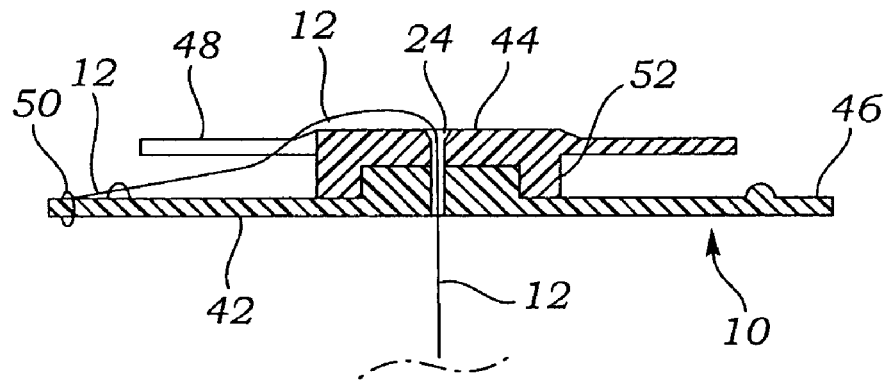
FIG. 3B depicts a side view, in partial cross section, of the apparatus of FIG. 3A.

In the embodiment of FIGS. 3A and 3B, the spindle 50 includes an outer circumference 54 having notches 56. These notches 56 can be used to secure the upper rotatable portion 44 in a fixed position. For example, once the desired tension in the tensioning line 12 was achieved, the user could secure a suture line to a part of the fixed lower portion (such as one of the suture holes 46), then run that suture line across the upper portion 44 and though one or more of the notches 56, and then return the line to the fixed lower portion to be tied off. A suture line thus installed would prevent unwanted rotation of the upper portion 44.

The upper portion 44 can be configured to be easily snapped off of or otherwise removed from the lower portion 42, thus allowing the user to remove and/or replace the upper portion when necessary and/or convenient during a particular procedure. For example, a user could initially disassemble the device prior to installation, and then pass the tensioning element out of the organ, thread the tensioning element through the lower portion, secure the lower portion to the organ wall, thread the tensioning element through the upper portion, secure the upper portion to the lower portion, and then adjust the tension in the tensioning element. The user could also remove the upper portion after the lower portion was already secured to the organ wall.

FIGS. 4A and 4B depict a further embodiment of the invention where an adjustable support pad 10 includes a base portion 60 having a rotatable upper portion 62. In the particular embodiment depicted, the tensioning line would be passed through the pad hole 24, passes over the top of the rotatable upper portion 62 through a tensioning line groove 63 and down through a slot 64, and is secured to the rotatable upper portion 62 at one or more suture tie-off holes 66. Note that these same tie-off holes 66 can also be used to secure the adjustable pad 10 to the surface of a body organ via suture.

The rotatable upper portion 62 is rotated, causing the tensioning line 12 to wrap around the spool 68 and thereby adjusting the tension in the tensioning line 12. In the embodiment of FIGS. 4A and 4B, there is a ratchet-like structure 70 on the rotatable upper portion 62 that allows the rotatable upper portion 62 to be rotated in a first rotatable direction 72, but prevents rotatable movement of the rotatable upper portion 62 in a second rotatable direction 74. The ratchet-like structure 70, depicted in greater detail in FIG. 4C, includes an arm 76 having an angled downward projection 78 at its end. The angled downward projection 78 has flat face 80 on one side and an angled face 82 on an opposing side. When the upper portion 62 is secured to the base portion 60, the angled downward projection 78 lodges within gear-like recesses 84 formed in the base portion 60 in a circular pattern of which at least a portion lies underneath the angled downward projection 78 when the upper portion 62 is secured to the base portion 60. When the rotatable upper portion 62 is rotated in the first rotatable direction 72, the angled face 82 is presented to the gear-like recesses 84, which allows the rotatable upper portion 62 to rotate as the angled face 82 rises and falls over the gear-like recesses 84. When the rotatable upper portion 62 is rotated in the second rotatable direction 74, the flat face 80 is presented to the gear-like recesses 84, which prevents rotation of the rotatable upper portion 62 due to the engagement of the flat face 80 against corresponding surfaces of the gear-like recesses 84. Note that the user can manually release the ratchet mechanism by lifting the arm 76 until the angled downward projection 78 is clear of the gear-like recesses 84, at which point the upper rotatable portion 62 may be rotated in either direction 72, 74.

The embodiment depicted in FIG. 4A also includes locking suture holes 86a, 86b on the rotatable upper portion 62, with a suture-receiving groove 87 passing therebetween. A user can lock the rotatable upper portion 62 in place to prevent rotation in either rotatable direction 72, 74 by passing a line of suture from one of the suture tie-off holes 66a, up through a first locking suture hole 86a, across a suture groove 87 in the top of the rotatable upper portion 62, back through a second locking suture holes 86b, and then to another of the suture tie-off holes 66b. In the embodiment depicted, the suture groove 87 passes over the tensioning line groove 63, so that a suture tightened across the suture groove 87 will engage the portion of the tensioning line passing through the tensioning line groove 63. With the suture tightened and tied off at either end to the suture tie-off holes 66a, 66b, the suture will thus prevent rotation of the rotatable upper portion in either direction 72, 74, while also providing some resistance against sliding of the tensioning line through the tensioning line groove 63.

Figure 5:
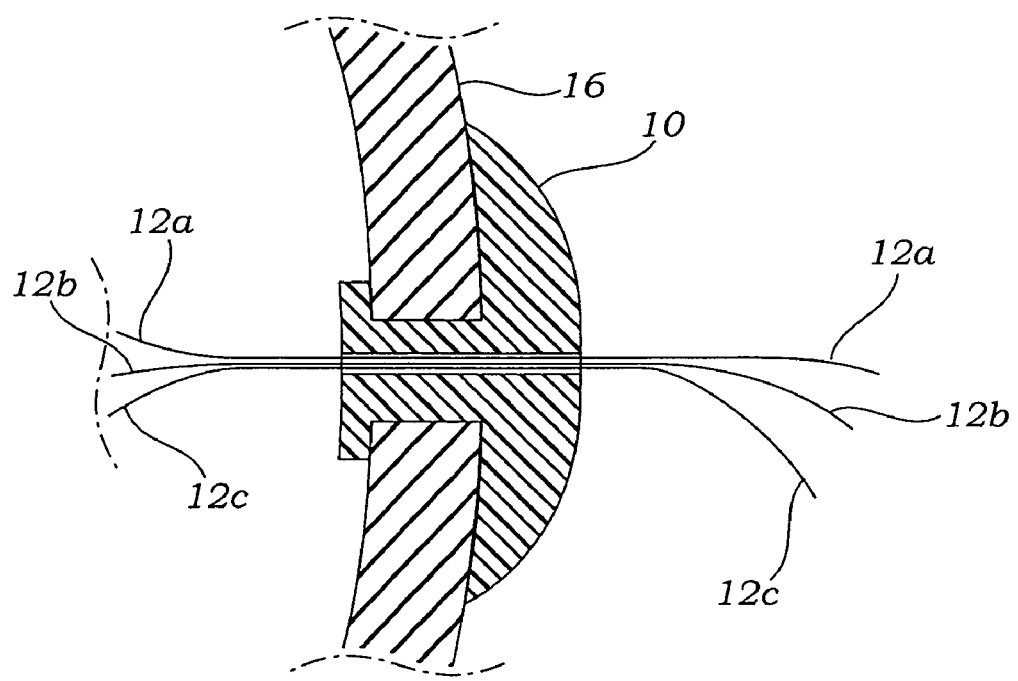
FIG. 5 depicts a side view, in partial cross-section, of a further embodiment of the invention.

Depending on the particular application, one or more tensioning lines can be secured to a single adjustable support pad. For example, in the device depicted in FIG. 5, multiple tensioning lines 12a, 12b, 12c are slidably secured to a single adjustable support pad 10. The multiple tensioning lines 12a, 12b, 12c can be secured in place to prevent sliding in one or more directions using locking mechanisms such as those discussed above.

Figure 6:
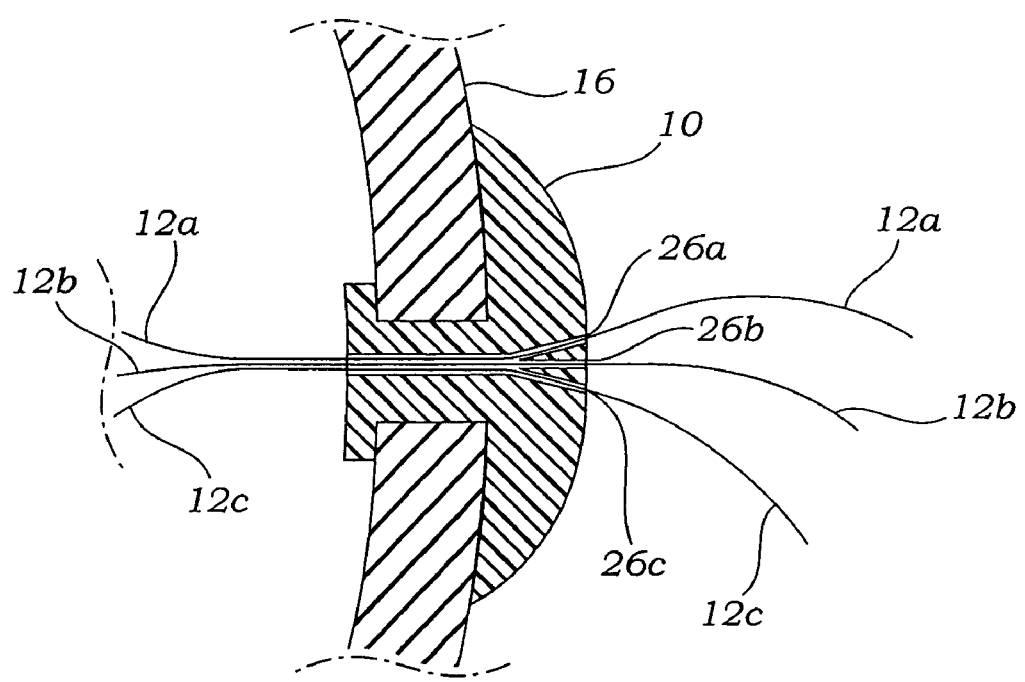
FIG. 6 depicts a side view, in partial cross-section, of a further embodiment of the invention.

In a further embodiment such as that depicted in FIG. 6, a single adjustable support pad 10 includes multiple locking mechanisms 26a, 26b, 26c, each of which can secure one or more tensioning lines 12a, 12b, 12c. Such an embodiment can be particularly useful for applications where there is a need for multiple tensioning lines that must be individually secured and adjusted at a position where there is limited room for adjustable support pads. By separating the locking mechanisms on a single pad, the tension of one or more individual tensioning lines can be easily adjusted without interfering with the tension in one or more of the other tensioning lines secured to other locking mechanisms.

The adjustable support pad can be formed from various biocompatible materials, including metals, polymers, ceramics, and/or composites. The adjustable support pad can also be configured to conform to the body organ. For example, an adjustable support pad for use in replacing chordae tendineae can be configured to conform to the outer surface of the human heart, such as an outer surface at or adjacent the apex of the heart. Such an adjustable support pad could, for example, be initially formed having an organ-facing surface that generally matches the corresponding outer surface of the heart to which the adjustable support pad will be secured. The adjustable support pad can be formed as a rigid structure, or can be formed as a generally flexible structure that can flex to modify its shape to better conform to the body organ of the particular application.

The tensioning element can take various forms. It may be a common suture. For applications where the tension was desired to be temporary, or where body tissue was expected to grow and take over the role of applying the tension, the tensioning line and/or adjustable support pad could be formed from material that is absorbed over time. For other applications, however, the tensioning line and/or adjustable support pad can be formed from non-absorbable material. The tensioning element can also contain bumps, ridges, or gears to facilitate one-directional tensioning against a locking mechanism, and could allow for the release of such tensioning.

The tensioning line can include a shock absorbing component positioned between the adjustable support pad 10 and the tensioning line attachment point 20 on the organ 14, such as the nitinol spring 88 depicted in the tensioning line 12 of FIG. 7, which may be particularly useful for an organ that may flex and/or otherwise deform in shape to the point where tension on a regular tensioning line might become excessive during organ deformation. In the case of a tensioning line being used as a replacement for chordae tendineae, the shock absorbing mechanism could be used to mimic the effect of the papillary muscle or muscles.

FIG. 8 depicts an adjustable support pad used to implant a tensioning line in the form of a replacement chordae 90 in a heart 92. A first end 94 of the replacement chordae 90 has been attached to a heart valve leaflet 96. An adjustable support pad 10 has been secured to the heart outer surface 98, with the flange 32 and pad hole 24 penetrating the heart wall 100. In the embodiment depicted, the adjustable support pad 10 is positioned adjacent the lower portion of the heart ventricle 102 and adjacent the apex 104, which will approximate the attachment position of the native chordae being replace in this embodiment, which would have been attached to the papillary muscle which in turn is attached to the heart in the lower ventricular portion. The replacement chordae 90 has been passed through the heart wall 100 and into the pad hole 24 of the adjustable support pad 10.

Note that the order of the steps discussed above could be varied. For example, the replacement chordae could be initially secured to the adjustable support pad 10, then passed through the heart wall 100 and secured to the valve leaflet 96. Also, the steps could be performed on a beating heart, and/or on an arrested heart with the patient on bypass.

With the replacement chordae 90 and adjustable support pad 10 in place, the tension in the replacement chordae 90 can be adjusted to the desired level. Adjusting the tension may preferably be performed on a beating heart, but in some applications the heart may need to be arrested depending on patient condition, etc. Adjusting the tension may be performed concurrently with monitoring of the heart and valve performance, which can be monitored by an imaging technique such as echocardiography. In the embodiment of FIG. 8, an imaging system 106 provides real-time imaging of the heart and valve, with an imaging device 108 such as an ultrasound transducer providing a signal that is processed into images displayed on a display 110. The user can adjust the tension while concurrently monitoring the performance of the heart valve. Note that concurrently can include, but does not require, simultaneous monitoring and tensioning adjustment. For example, a user may concurrently adjust the tension and monitor heart/valve performance by making an initial adjustment to the tension, pausing to monitor the heart/valve performance on the imaging system, then make an additional adjustment to the tension based on the monitored heart valve performance, then pause again to monitor the performance, etc. After the desired tension is achieved and the replacement chordae 90 is secured in the adjustable support pad 10, any excess replacement chordae 90 (i.e., the slack portion 30) can be cut off.

Figure 9:
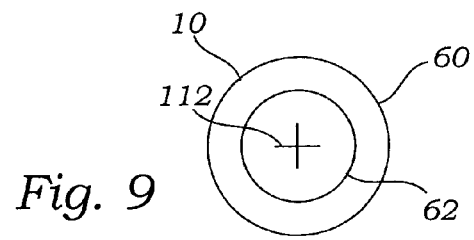
FIG. 9 depicts a top view of a further embodiment of the invention.

Various methods and devices can be used to adjust and/or maintain the tension. For example, the support pad may include a connecting and/or receiving assembly/device for receiving an adjustment tool that can adjust the tension. As an example, a support pad having a rotatable tensioning adjustment mechanism, such as device discussed and depicted with respect to FIGS. 4A, and 4B, could utilize a flat-head or Philips screwdriver-type connection, so that the user could use a simple screwdriver to rotate the rotatable tensioning adjustment mechanism. Such a support pad 10 is depicted in FIG. 9, with a base portion 60 and rotatable portion 62, wherein the rotatable portion 62 includes a generally cross-shaped indentation 112 configured to receive a Philips-head screwdriver tip. Other adjustment tools and connections are also within the scope of the invention, such as an adjustment tool that can be easily connected to and disconnected from the support pad.

Figure 10A:
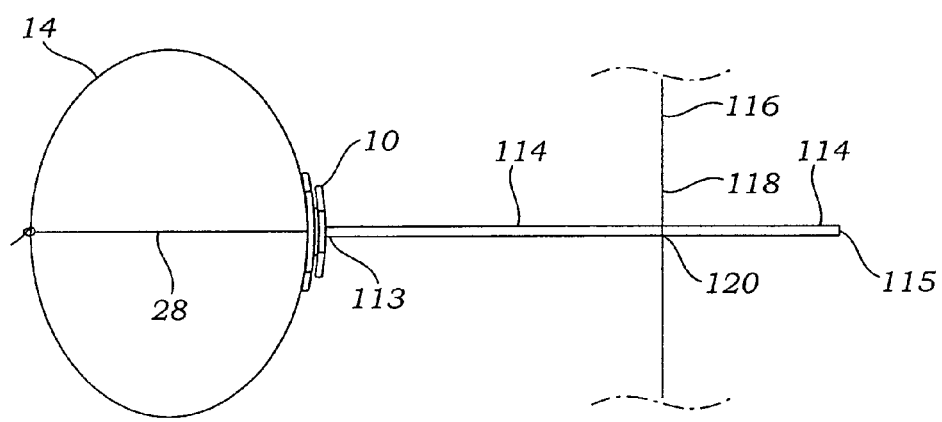
FIGS. 10A and 10B depict side views, in partial cross-section, of a further embodiment of the invention.
Figure 10B:
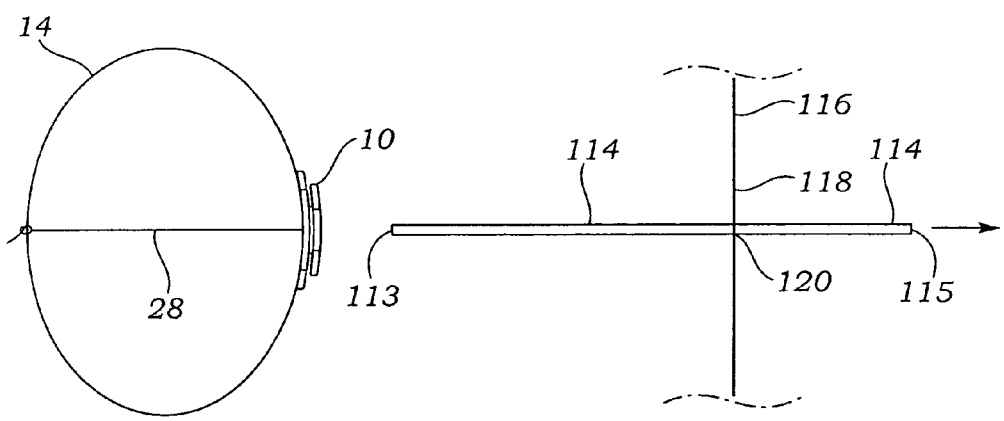

Another tool for adjusting tension may be an elongated adjustment element 114, such as a flexible adjustment wire or rod, that can remain permanently or removably attached to the support pad 10 at a distal end 113 end with the proximal end 115 extending outside of the patient's body 116 through the patient's skin 118, as depicted in FIG. 10A. The surgeon or other user can complete the installation of the support pad 10 (which may include making initial tensioning adjustments to the tensioning element), and then close up the surgical openings in the patient except for a small opening 120 (e.g., a port) out of which the elongated adjustment element 114 would extend. The user could thus adjust the tension during and after the procedure wherein the adjustable pad 10 was installed. For example, the patient may recover for a period, and then the surgeon or other user could re-examine the patient (possibly including imaging or other assessment of the patient's heart function) and perform tensioning adjustments externally in accordance with the reexamination. The device could also include an apparatus and method for remotely disconnecting the elongated adjustment element 114 from the support pad 10, so that once the surgeon or user is satisfied with the tensioning, the elongated adjustment element 114 could be remotely disconnected from the support pad 10 and removed from the patient 116 without performing major surgery, as depicted in FIG. 10B.

Figure 11A:
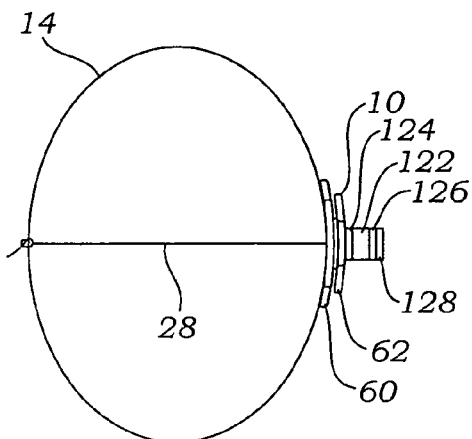
FIGS. 11A through 11C depict side views, in partial cross-section, of further embodiments of the invention.

Another device and method for adjusting the tension can include the use one or more small motors, such as an electric motor 122, that can be included in the support pad 10 itself, as in FIG. 11A. As depicted in FIG. 11A, the support pad 10 may also include one or more sensors 124 to monitor tension, one or more controllers 126 (such as microprocessors) to process tension signals and control the motor 122 to adjust the tension, and or more batteries 128 to power the motor 122, controller 126, and/or sensor 124.

Figure 11B:
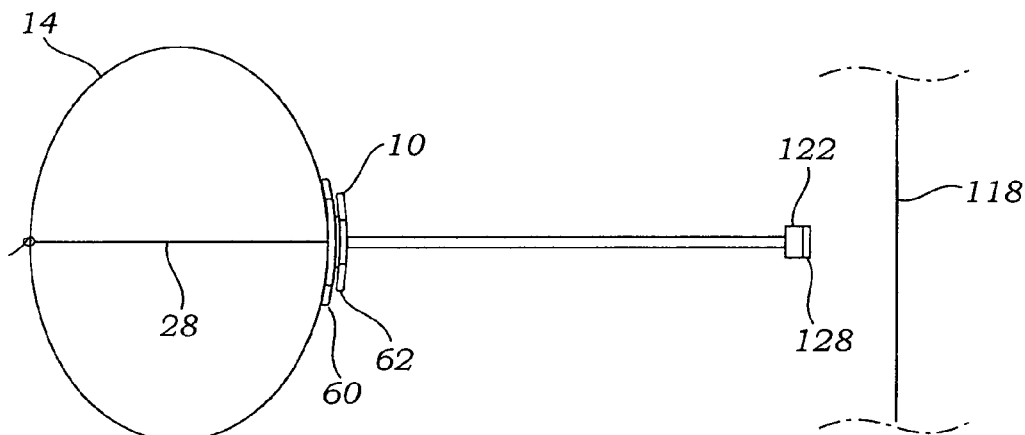

In another embodiment, depicted in FIG. 11B, the electric motor 122 and battery 128 are located some distance from the support pad 10, such as at a location on or near the surface of the patient's skin 118. In the embodiment depicted in FIG. 11B, an electric motor 122 is located under but adjacent the patient's skin 118 and other external tissue, in a fashion similar to the locating of modern pacemakers. The electric motor 122 is connected to the support pad 10 via a elongated shaft 130, which can be flexible or rigid and, in the embodiment depicted in FIG. 11B, serves to translate motor rotation into rotation of the rotatable portion 62 of the particular support pad 10 depicted. In such an embodiment, the controller and/or sensor (not depicted), if present, can be located with the support pad 10, with the battery 128 and/or motor 122, or elsewhere.

Figure 11C:
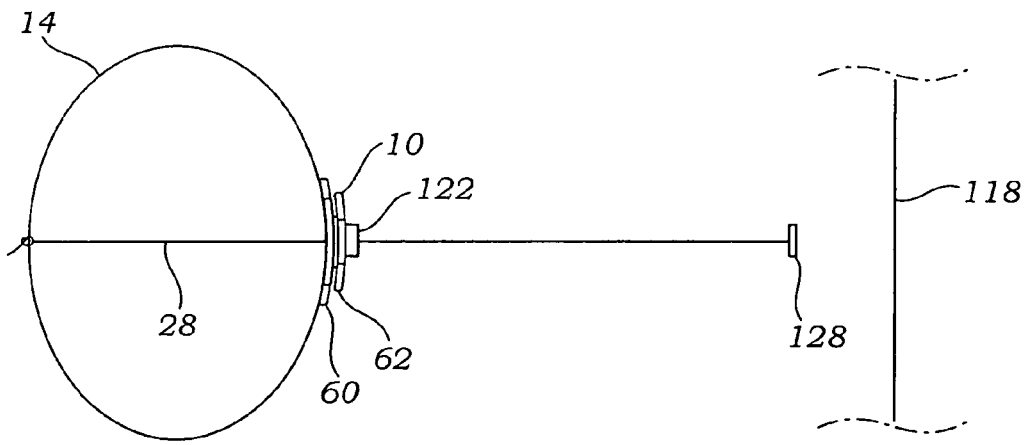

Another embodiment is depicted in FIG. 11C, wherein the motor 122 itself is located in the adjustable support pad 10, but the battery 128 to power the motor 122 is positioned remotely under the patient's skin 118 and external tissue. The battery 128 provides electricity to the motor 122 via one or more small wires 132. In such an embodiment, the motor controls and/or tension sensors (if present) could be located with the battery 128, with the motor 122 and/or adjustable support pad 10, or at another location, depending on the particular application.

As discussed above, the operation of the tensioning adjustment motor could be controlled by circuitry or other controls located on or in the support pad itself or co-located with the battery and/or motor, and/or could be controlled remotely by a surgeon or other user, or by a remote computer, or by combinations thereof, etc. In the case of the control system being remotely located, the remote control signals could be wirelessly transmitted, such as via radio signals, or could be transmitted through small transmittal lines, such as wires and/or fiber-optic lines, that extend from the adjustment motor to a location outside of, or just inside of, the patient's body. For example, in the embodiment depicted in FIG. 11B, the motor 122 could be controlled, and/or the controller (if present) could be reprogrammed, and/or the battery 128 could be recharged (where run by batteries), remotely using technology similar to that used to control and/or recharge pacemaker/defibrillator controls and batteries. For example, in the embodiment of FIGS. 11B and 11C, the batteries could be recharged using magnetic induction by placing a charging element next to the patient's skin 118 in the area adjacent the battery 128.

Figure 12A:
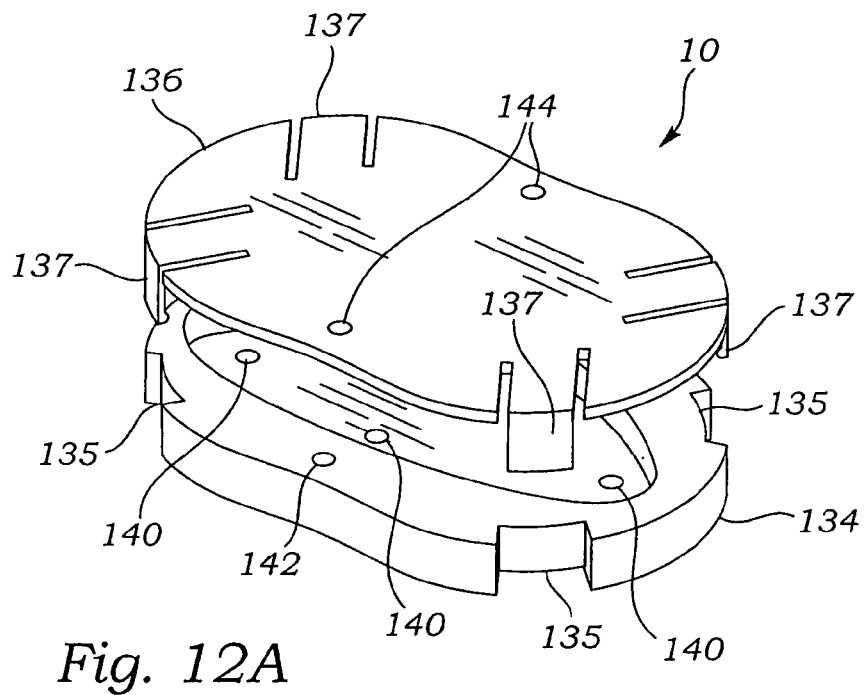
FIGS. 12A and 12B depict perspective views of further embodiments of the invention.
Figure 12B:
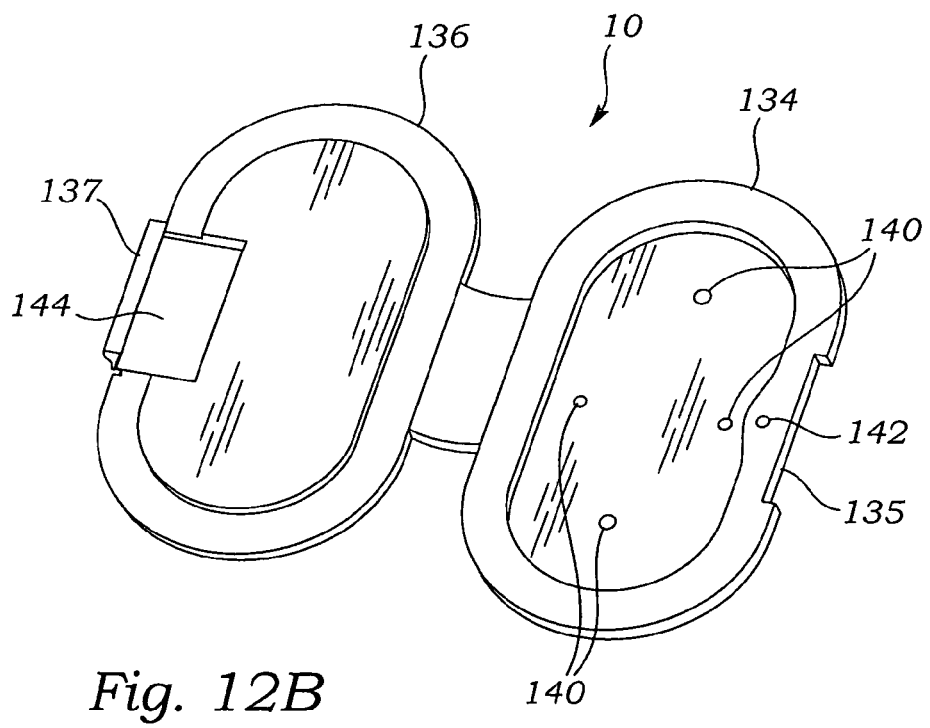

FIGS. 12A and 12B depict further embodiments of the invention, with an adjustable support pad 10 having a base portion 134 and a snap-on portion 136. In the embodiment of FIG. 12A, the snap-on portion 136 is initially free and unattached from the base portion 134. In the embodiment of FIG. 12B, the snap-on portion 136 is movably secured to the base portion 134 via a hinge 138. The snap-on portion 136 includes one or more snap engaging structures 137 which align with and engage into corresponding recesses 135 in the base portion 134 when the snap-on portion 136 is snapped onto the base portion 134. In the particular embodiment depicted on FIGS. 12A and 12B, there are multiple holes 140 passing through the base portion 134. Depending on the particular application, one or more of the holes 140 can serve as suture holes through which ordinary suture can be used to fasten the support pad 10 to the organ wall, and/or one or more of the holes 140 can serve as pad holes through which a tensioning line (such as the suture line 12 of FIG. 1) is passed. With the base portion 134 secured to the organ and the tensioning line passed through the pad hole 24, the user adjusts the tension in the tensioning line to the desired level and then secures the tensioning line to prevent further movement to preserve the desired tension.

The tensioning line can be secured in various ways, depending on the particular application and support pad. For example, the tensioning line could be tied off at the desired tension, and/or one or more portions of the tensioning line could be passed between the base portion 134 and the snap-on portion 136 such that the tensioning line is held firmly in place between the base portion 134 and snap-on portion 136 once the snap-on portion 136 is snapped onto the base portion 134. One or more portions of the tensioning line could be wrapped around part of the base portion 134 and/or snap-on portion 136 to increase the strength of the locking action on the tensioning line created by snapping the snap-on portion 136 onto the base portion 134. Where the locking of the tensioning line is accomplished by snapping the snap-on portion 136 onto the base portion 134, the surgeon or other user can adjust the tension in the tensioning line to a desired level, and then snap the snap-on portion 136 onto the base portion 134, thereby creating a lock that prevents the tensioning line from further movement and preserves the desired tension. The surgeon or other user can re-adjust the tension by re-opening the support pad 10 (by snapping the snap-on portion 136 off of the base portion 134), readjusting the tension in the tensioning line, and then snapping the snap-on portion back onto the base portion 134 to re-establish the locking action that prevents further movement of the tensioning line.

The support pads 10 of FIGS. 12A and 12B include locking lower suture holes 142 and locking upper suture holes 144 in the base portion 134 and snap-on portion 136, respectively. The upper and lower locking suture holes 142, 144 align when the snap-on portion 136 is properly secured to the base portion 134, and a user can pass ordinary suture through the aligned upper and lower suture holes 142, 144 and tie off the suture to lock the snap-on portion 136 onto the base portion 134 in its closed configuration.

Note that a lid-like structure such as the snap-on portion 136 of FIGS. 12a and 12b could be used in combination with the locking mechanisms set forth in other embodiments of the invention, with the lid-like structure acting to protect and/or support the locking mechanism and/or other elements of the support pad. For example, a lid-like mechanism could be combined with the support pad 10 depicted in FIG. 4A, with the lid-like mechanism acting to hold the rotatable upper portion 62 in place and prevent further rotation when the lid-like structure is snapped-on and/or otherwise secured onto the base portion 60 of the support pad 10 of FIG. 4A.

While the invention has been described with reference to particular embodiments, it will be understood that various changes and additional variations may be made and equivalents may be substituted for elements thereof without departing from the scope of the invention or the inventive concept thereof. For example, while the invention is specifically discussed in application with repair and/or replacement of chordae tendineae, it has applicability in other areas where it is desired to repair similar structures. In addition, many modifications may be made to adapt a particular situation or material to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A method for replacing a chordae tendon in a heart, the heart having an apex, a native valve leaflet, a ventricle, and a heart wall, the method comprising:

providing a replacement chordae tendinae assembly, the assembly comprising: (a) a tensioning line having a first end portion and a second end portion, wherein the first end portion is configured for attachment to a native valve leaflet; and (b) an adjustable support pad configured for attachment to a heart wall, the adjustable support pad comprising a first surface configured to be placed against and secured to the heart wall, the adjustable support pad configured to receive the tensioning line therethrough and including a locking mechanism configured to slidingly receive the tensioning line in a first direction with respect to the adjustable support pad, and to prevent the tensioning line from sliding in a second direction with respect to the adjustable support pad, wherein the first direction is opposite to the second direction;

passing the tensioning line into the ventricle by passing the tensioning line through the heart wall adjacent the ventricle;

securing the first end portion of the tensioning line to the native valve leaflet;

sliding the second end portion of the tensioning line through the adjustable support pad;

securing the adjustable support pad to the heart wall at a lower portion of the ventricle of the heart;

adjusting the length of the portion of the tensioning line which extends from the adjustable support pad to the native valve leaflet; and locking the locking mechanism onto the tensioning line to prevent the tensioning line from further sliding through the adjustable support pad.

2. The method of claim 1, wherein the adjustable support pad is configured for attachment to an external surface of the heart wall, and wherein securing the adjustable support pad to the heart wall comprises securing the adjustable support pad to an exterior surface of the heart wall at a position adjacent the apex of the heart.

3. The method of claim 1, wherein the adjustable support pad comprises a plurality of suture openings therethrough, wherein the plurality of suture openings are positioned at or adjacent a perimeter of the adjustable support pad, and wherein securing the adjustable support pad to the heart wall comprises suturing the adjustable support pad to the heart wall using sutures passing through one or more of the plurality of suture openings.

4. The method of claim 1, wherein the locking mechanism has an unlocked configuration wherein the tensioning line can slidingly move in the first direction, and a locked configuration wherein the tensioning line is prevented from moving in the second direction, wherein adjusting the length of the portion of the tensioning line which extends from the adjustable support pad to the native valve leaflet comprises slidingly moving the tensioning line in the first direction.

5. The method of claim 4, wherein the locking mechanism in the unlocked configuration allows movement of the tensioning line in the second direction, and wherein adjusting the length of the portion of the tensioning line which extends from the adjustable support pad to the native valve leaflet comprises moving slidingly the tensioning line in the second direction.

6. The method of claim 4, wherein the locking mechanism in the locked configuration prevents movement of the tensioning line in the first direction, and wherein locking the locking mechanism onto the tensioning line comprises moving the locking mechanism from an unlocked configuration to a locked configuration.

7. The method of claim 1, wherein the tensioning line comprises a shock absorbing component.

8. The method of claim 7, wherein the shock absorbing component comprises a spring.

9. The method of claim 1, wherein the adjustable support pad comprises a pre-formed pad hole configured to receive the tensioning line therethrough, and wherein sliding the second end portion of the tensioning line through the adjustable support pad comprises sliding a portion of the tensioning line through the pre-formed pad hole.

10. The method of claim 1, wherein the adjustable support pad comprises a generally compressible and solid material configured to receive a suturing needle and suturing line therethrough, and wherein securing the adjustable support pad to the heart wall comprises suturing the adjustable support pad to the heart wall using the suturing needle to pass the suture line through the generally compressible and solid material.

11. A method of replacing a chordae tendon in a heart, comprising:
  securing a first portion of a replacement chordae tendon to a heart valve leaflet;
  securing an adjustable support pad to an exterior surface of a heart wall of the heart;
  passing the replacement chordae tendon through the heart wall;
  adjusting tension in the replacement chordae tendon from outside the heart wall by proximally or distally moving a second portion of the replacement chordae tendon; and
  securing the second portion of the replacement chordae tendon to the support pad.

12. The method of claim 11, further comprising:
  monitoring blood flow function of the heart valve while the heart is beating while concurrently adjusting tension in the replacement chordae tendon.

13. The method of claim 12, wherein monitoring the blood flow function of the heart valve comprises monitoring the function of the heart valve using an imaging system.

14. The method of claim 11, wherein securing the support pad to the exterior surface of the heart wall of the heart comprises securing the support pad adjacent the apex of the heart.

15. The method of claim 11, wherein securing the first portion of the replacement chordae tendon to the heart valve leaflet occurs prior to securing the second portion of the replacement chordae tendon to the support pad.

16. The method of claim 11, wherein adjusting tension in the replacement chordae tendon from outside the heart wall comprises adjusting tension while the heart is beating.

17. A method for replacing a chordae tendon in a heart having a native valve leaflet, a ventricle, and a heart wall, the method comprising:
  providing an the apparatus comprising: (a) a tensioning line; (b) an adjustable support pad comprising a first surface configured to be secured to a heart wall, the adjustable support pad further comprising an adjustable tensioning element configured to move with respect to the adjustable support pad, the adjustable support pad configured to receive and movably hold a portion of the tensioning line via movement of the adjustable tensioning element; and (c) a controller for controlling movement of the adjustable tensioning element;
  passing the tensioning line into the ventricle by passing the tensioning line through the heart wall adjacent the ventricle;
  securing a first end portion of the tensioning line to the native valve leaflet;
  sliding a second end portion of the tensioning line through the adjustable support pad;
  securing the first surface of the adjustable support pad to the heart wall at a lower portion of the ventricle of the heart; and
  selectively adjusting tension in the tensioning line by selectively moving the adjustable tensioning element to control sliding movement of the second end portion of the adjustable tensioning line through the adjustable support pad.

18. The method of claim 17, wherein the controller comprises a motor, and wherein the step of selectively adjusting tension in the tensioning line by selectively moving the adjustable tensioning element comprises activating the motor to initiate movement of the adjustable tensioning element.

19. The method of claim 18, wherein the motor is positioned on or in the adjustable support pad.

20. The method of claim 17, wherein the adjustable tensioning element is configured for rotational movement, and wherein the step of selectively adjusting tension in the tensioning line by selectively moving the adjustable tensioning element comprises selectively rotating the tensioning element.

* * * * *